United States Patent
Augustine et al.

(10) Patent No.: US 8,257,328 B2
(45) Date of Patent: Sep. 4, 2012

(54) PORTABLE NEGATIVE PRESSURE WOUND THERAPY DEVICE

(75) Inventors: James Augustine, Bridgewater, MA (US); Scott Wudyka, Marborough, MA (US); William Durkin, Appleton, WI (US); Steven Kleis, Sherwood, WI (US)

(73) Assignee: Tyco Healthcare Group LP, Mansfield, MA (US)

( * ) Notice: Subject to any disclaimer, the term of this patent is extended or adjusted under 35 U.S.C. 154(b) by 536 days.

(21) Appl. No.: 12/486,379

(22) Filed: Jun. 17, 2009

(65) Prior Publication Data

US 2010/0010477 A1    Jan. 14, 2010

Related U.S. Application Data

(60) Provisional application No. 61/078,838, filed on Jul. 8, 2008.

(51) Int. Cl.
*A61M 1/00* (2006.01)

(52) U.S. Cl. .......................................... 604/313; 604/319

(58) Field of Classification Search .................... 604/67, 604/305, 313, 317–319, 321, 327, 331; 137/625.43
See application file for complete search history.

(56) References Cited

U.S. PATENT DOCUMENTS

| | | |
|---|---|---|
| 3,026,874 A | 3/1962 | Stevens |
| 3,367,332 A | 2/1968 | Groves |
| 3,486,504 A | 12/1969 | Austin, Jr. |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,202,331 A | 5/1980 | Yale |
| 4,224,945 A | 9/1980 | Cohen |
| 4,228,798 A | 10/1980 | Deaton |
| 4,266,545 A | 5/1981 | Moss |
| 4,280,680 A | 7/1981 | Payne |

(Continued)

FOREIGN PATENT DOCUMENTS

DE    41 11 122 A1    4/1993

(Continued)

OTHER PUBLICATIONS

Björn, et al., "Irrigation Treatment in Split-thickness Skin Grafting of Intractable Leg Ulcers," Scand J Plast Reconstr Surg 19: 211-213, 1985.

(Continued)

*Primary Examiner* — Melanie Hand

(57) ABSTRACT

A portable NPWT system includes a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister has ports to introduce a vacuum from the vacuum source into the collection canister. A ball float is provided to substantially close the suction port in response to one of collection of a predetermined volume of exudate in the collection canister, tilting of the collection canister beyond a predetermined angle of orientation or inversion of the collection canister.

11 Claims, 10 Drawing Sheets

U.S. PATENT DOCUMENTS

| | | |
|---|---|---|
| 4,382,441 A | 5/1983 | Svedman |
| 4,510,802 A | 4/1985 | Peters |
| 4,524,064 A | 6/1985 | Nambu |
| 4,538,645 A | 9/1985 | Perach |
| 4,655,754 A | 4/1987 | Richmond et al. |
| 4,700,479 A | 10/1987 | Saito et al. |
| 4,710,165 A | 12/1987 | McNeil et al. |
| 4,738,257 A | 4/1988 | Meyer et al. |
| 4,743,232 A | 5/1988 | Kruger |
| 4,870,975 A | 10/1989 | Cronk et al. |
| 4,874,363 A | 10/1989 | Abell |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,135,485 A | 8/1992 | Cohen et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,180,375 A | 1/1993 | Feibus |
| 5,195,977 A | 3/1993 | Pollitt |
| 5,261,893 A | 11/1993 | Zamierowski |
| 5,263,922 A | 11/1993 | Sova et al. |
| D364,679 S | 11/1995 | Heaton et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,624,374 A | 4/1997 | Von Iderstein |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,779,657 A | 7/1998 | Daneshvar |
| 5,787,928 A * | 8/1998 | Allen et al. ............... 137/625.43 |
| 5,840,049 A | 11/1998 | Tumey et al. |
| 5,911,222 A | 6/1999 | Lawrence et al. |
| 5,944,703 A | 8/1999 | Dixon et al. |
| 5,960,837 A | 10/1999 | Cude |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| D434,150 S | 11/2000 | Tumey et al. |
| 6,142,982 A | 11/2000 | Hunt et al. |
| 6,174,306 B1 | 1/2001 | Fleischmann |
| 6,203,563 B1 | 3/2001 | Fernandez |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| D469,175 S | 1/2003 | Hall et al. |
| D469,176 S | 1/2003 | Hall et al. |
| 6,520,982 B1 | 2/2003 | Boynton et al. |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| D478,659 S | 8/2003 | Hall et al. |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Bybordi et al. |
| 6,994,702 B1 | 2/2006 | Johnson |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 2001/0020145 A1 | 9/2001 | Satterfield et al. |
| 2001/0031943 A1 | 10/2001 | Urie |
| 2001/0043943 A1 | 11/2001 | Coffey |
| 2002/0016577 A1 | 2/2002 | Ohmstede |
| 2002/0108614 A1 | 8/2002 | Schultz |
| 2002/0143286 A1 | 10/2002 | Tumey |
| 2002/0151836 A1 | 10/2002 | Burden |
| 2002/0161346 A1 | 10/2002 | Lockwood et al. |
| 2002/0198504 A1 | 12/2002 | Risk, Jr. et al. |
| 2003/0078532 A1 | 4/2003 | Ruszczak et al. |
| 2003/0093041 A1 | 5/2003 | Risk, Jr. et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |

| | | |
|---|---|---|
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risks, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 | 5/2005 | McCraw |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0039742 A1 | 2/2006 | Cable, Jr. et al. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0066946 A1 | 3/2007 | Haggstrom et al. |
| 2007/0078366 A1 | 4/2007 | Haggstrom et al. |
| 2007/0078432 A1 | 4/2007 | Halseth et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0219513 A1 | 9/2007 | Lina et al. |
| 2007/0225663 A1 | 9/2007 | Watt et al. |
| 2007/0233022 A1 | 10/2007 | Henley et al. |
| 2007/0265585 A1* | 11/2007 | Joshi et al. .................. 604/313 |
| 2008/0011667 A1 | 1/2008 | Ruschke |
| 2008/0071235 A1 | 3/2008 | Locke et al. |
| 2008/0082059 A1* | 4/2008 | Fink et al. .................. 604/305 |
| 2008/0103462 A1 | 5/2008 | Wenzel et al. |
| 2008/0132819 A1 | 6/2008 | Radl et al. |
| 2008/0167593 A1 | 7/2008 | Fleischmann |
| 2008/0183233 A1 | 7/2008 | Koch et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |

FOREIGN PATENT DOCUMENTS

| | | |
|---|---|---|
| DE | 43 06 478 | 9/1994 |
| DE | 295 04 378 U1 | 10/1995 |
| EP | 0 358 302 | 3/1990 |
| EP | 1 088 569 | 4/2001 |
| EP | 1 219 311 | 8/2002 |
| EP | 0 853 950 B1 | 10/2002 |
| GB | 488 232 | 7/1938 |
| GB | 1 415 096 | 11/1975 |
| GB | 1 549 756 | 3/1977 |
| GB | 2 195 255 A | 4/1988 |
| GB | 2 235 877 A | 3/1991 |
| GB | 2 307 180 | 5/1997 |
| GB | 2 329 127 | 3/1999 |
| GB | 2 336 546 | 10/1999 |
| GB | 2 244 531 | 6/2000 |
| GB | 2 415 908 | 1/2006 |
| SU | 1 762 940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1990 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 00/21586 | 4/2000 |
| WO | WO 03/005943 | 1/2003 |
| WO | WO 03/018098 | 3/2003 |
| WO | WO 03/030966 | 4/2003 |
| WO | WO 03/057070 | 7/2003 |
| WO | WO 03/057071 | 7/2003 |
| WO | WO 03/057307 | 7/2003 |
| WO | WO 03/045492 | 8/2003 |
| WO | WO 03/086232 | 10/2003 |
| WO | WO 03/092620 | 11/2003 |
| WO | WO 03/101508 | 12/2003 |
| WO | WO 2004/018020 | 3/2004 |
| WO | WO 2005/009488 | 2/2005 |
| WO | WO 2006/015599 | 2/2006 |
| WO | WO 2006/105892 | 10/2006 |
| WO | WO 2008/020862 | 2/2008 |
| WO | WO 2008/048481 | 4/2008 |
| WO | WO 2008048481 A2 * | 4/2008 |

OTHER PUBLICATIONS

B.M. Kostiuchenok, et al., "The Vacuum Effect in the Surgical Treatment of Purulent Wounds," Russian Journal: Vestnik Khirurgii, Sep. 1986 (18-21).

Chardack, et al., "Experimental studies on Synthetic Substitutes for Skin and Their Use in the Treatment of Burns," vol. 155, No. 1 (128-136).

Chariker, M. E. et al. (eds), "Effective Management of Incisional and Cutaneous Fistulae with Closed Suction Wound Drainage," Contemporary Surgery, vol. 34, Jun. 1989, pp. 59-63.

H. Teder, et al., "Continuous Wound Irrigation in the Pig," Journal of Investigative Surgery, vol. 3 (399-407).

Jeter, Katherine F., et al., "Managing Draining Wounds and Fistulae: New and Established Methods", Chronic Wound Care, 1990, pp. 240-246.

Meyer, M.D., et al., "In Surgery, Medicine and the Specialties a Manual of its Practical Application", Bier's Hyperemic Treatment, Second Revised Edition, W.B. Saunders Company, 1909.

Mulder, G.D, et al., "Clinicians' Pocket Guide to Chronic Wound Repair," Wound Healing Publications Second Edition, 1991.

N.A. Bagautdinov (Kazan), "Variant of External Vacuum Aspiration in the Treatment of Pundent Diseases of Soft Tissues," UDC 616-002.36 (94-96).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

Paul Svedman, et al., "Staphylococcal Wound Infection in the Pig: Part I. Course," Annals of Plastic Surgery, vol. 23, No. 3, Sep. 1989 (212-218).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Sherry Stoll, "Energetic Remedies—Cupping: Healing Within a Vacuum," https://www.suite101.com/article.cfm/ energetic) remedies/74531, Apr. 13, 2005.

W. Fleischmann, "Vacuum Sealing for Treatment of Problematical Wounds", University Surgical Clinic and Polyclinic—Accident Surgery Department, WundForum Spezial—IHW 94.

W. Fleischmann, et al., Vacuum Sealing: Indication, Technique and Results, Emr J Orthop Surg Tramatol (1995) 5:37-40.

Y.N. Usupov, et al., "Active Wound Drainage," Russian Journal: Vestnik Khirugii, 1987, Apr. (42-45).

Yu A. Davydov, et al., "Bacteriological and Cytological Assessment of Vacuum Therapy of Purulent Wounds", Vestnik Khirurgii, Oct. 1988 (48-52).

Yu A. Davydov, et al., "Concepts for Clinical Biological Management of the Wound Process in the Treatment of Purulent Wounds Using Vacuum Therapy," Vestnik Khirugii, Feb. 1991, 132-135).

Yu A. Davydov, et al., "Vacuum Therapy in the Treatment of Purulent Lactation Mastitis," Russian Journal: Vesnik Khirurgii, Sep. 1986 (66-70).

Yu A. Davydov, et al., "Vacuum Therapy in treatment of Acute Purulent Diseases of Soft Tissues and Purulent Wounds," Vestnik Khirurgii, (Surgeon's Herald), MEDICINE Publishers, 1986.

Gorica Zivadinovic, et al., "Vacuum Therapy in the Treatment of Peripheral Blood Vessels," Conference Papers of the 5th Timok Medical Days, Majdanpek, 1986 (161-164).

US 6,216,701, 04/2001, Heaton et al. (withdrawn)

US 7,186,244, 03/2007, Hunt et al. (withdrawn)

* cited by examiner

PORTABLE NEGATIVE PRESSURE WOUND THERAPY DEVICE

CROSS-REFERENCE TO RELATED DOCUMENTS

The present invention claims the benefit of and priority to U.S. provisional patent Application Ser. No. 61/078,838, filed on Jul. 8, 2008, disclosure of which may be referred to herein by reference.

BACKGROUND

1. Technical Field

The present disclosure relates generally to treating a wound by applying negative pressure to the wound, and, more specifically, to a portable negative pressure wound therapy system for treating a wound.

2. Description of Related Art

Wound closure involves the migration of epithelial and subcutaneous tissue adjacent the wound towards the center and away from the base of the wound until the wound closes. Unfortunately, closure is difficult with large wounds, chronic wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Negative pressure wound therapy (NPWT), also known as suction or vacuum therapy, has been used in treating and healing wounds. Application of negative pressure, e.g. reduced or sub-atmospheric pressure, to a localized reservoir over a wound has been found to assist in closing the wound by promoting blood flow to the area, stimulating the formation of granulation tissue, and encouraging the migration of healthy tissue over the wound. Negative pressure may also inhibit bacterial growth by drawing fluids from the wound such as exudates, which may tend to harbor bacteria. This technique has proven particularly effective for chronic or healing-resistant wounds, and is also used for other purposes such as post-operative wound care.

Generally, negative pressure therapy provides for a wound covering to be positioned over the wound to facilitate suction at the wound area. A conduit is introduced through the wound covering to provide fluid communication to an external vacuum source. Atmospheric gas, wound exudates, or other fluids may thus be drawn from the reservoir through the fluid conduit to stimulate healing of the wound. Exudates drawn from the reservoir may be deposited in a collection canister.

Often, a portable NPWT device is worn by the patient so that the patient may remain ambulatory instead of being confined to a stationary position. While a patient is ambulatory, the portable NPWT device tends to tip or tilt in a multitude of directions. If there are enough exudates in the collection canister, the exudates may cover a suction port leading from the vacuum source to the collection canister because fluid In addition, portable NPWT devices have a control unit attached to the canister. The control unit generally contains the suction pump and sensitive electronics such as a pressure transducers, microprocessors, or the like. When the NPWT device tips, exudate may aspirate from the canister into the control unit thereby damaging the suction pump and/or electronic components.

SUMMARY

The present disclosure relates to a portable NPWT system including a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister has ports to introduce a vacuum from the vacuum source into the collection canister. A ball float is provided to substantially close the suction port in response to one of collection of a predetermined volume of exudate in the collection canister, tilting of the collection canister beyond a predetermined angle of orientation or inversion of the collection canister.

The present disclosure also relates to a portable NPWT system including a dressing assembly for positioning over a wound to apply a negative pressure to the wound and a canister assembly. The canister assembly includes a control unit having a vacuum source and a controller and a collection canister in communication with the dressing assembly operable to receive fluid from the wound. The collection canister has ports to introduce a vacuum from the vacuum source into the collection canister. A closure valve mounted adjacent to the suction port is provided and is adapted to move from an open position where the negative pressure source is capable of drawing a vacuum in the collection canister through the suction port and a closed position where the suction port is substantially closed in response to one of collection of a predetermined volume of exudate in the collection canister, tilting of the collection canister beyond a predetermined angle of orientation or inversion of the collection canister.

BRIEF DESCRIPTION OF THE DRAWINGS

Various embodiments of the wound dressing system of the present disclosure are described herein with reference to the drawings wherein.

DESCRIPTION OF THE PREFERRED EMBODIMENTS

Figure 1:
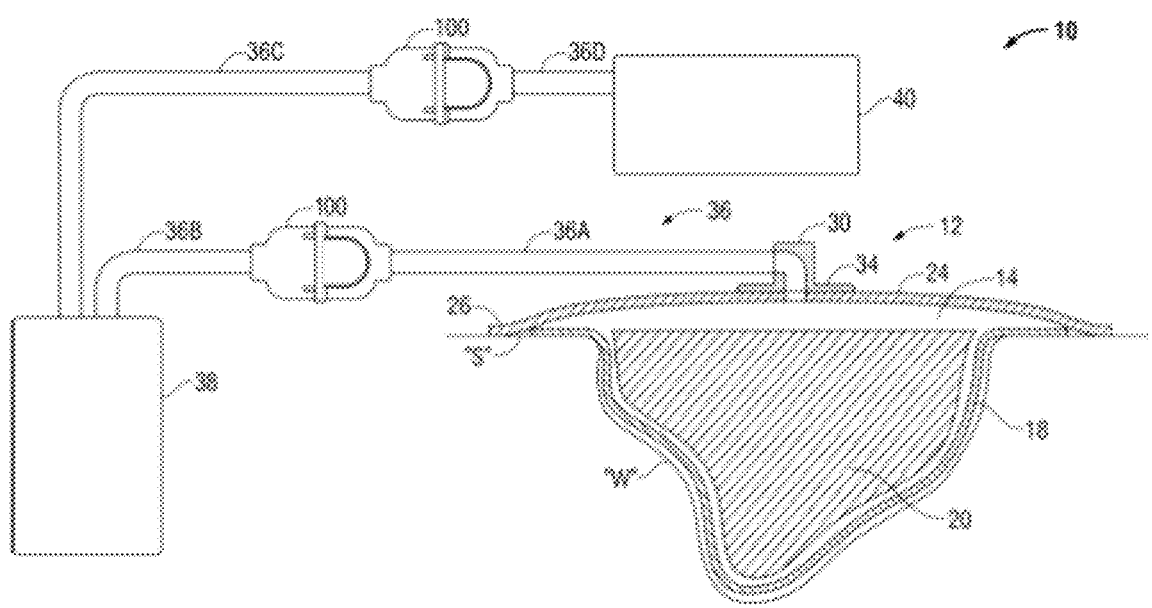
FIG. 1 is a diagram of an embodiment of a NPWT system in accordance with the present disclosure.

Various embodiments of the present disclosure provide NPWT systems (or apparatus) including a collection canister having a chamber to collect wound fluids. Embodiments of the presently disclosed NPWT systems are generally suitable for use in applying negative pressure to a wound to facilitate healing of the wound in accordance with various treatment modalities. Embodiments of the presently disclosed NPWT systems are entirely portable and may be worn or carried by the user such that the user may be completely ambulatory during the therapy period. Embodiments of the presently disclosed NPWT apparatus and components thereof may be entirely reusable or may be entirely disposable after a predetermined period of use or may be individually disposable whereby some of the components are reused for a subsequent therapy application.

Hereinafter, embodiments of the presently disclosed NPWT systems and embodiments of the presently disclosed sensors for use in NPWT systems will be described with reference to the accompanying drawings. Like reference numerals may refer to similar or identical elements throughout the description of the figures. As used herein, "wound exudate", or, simply, "exudate", generally refers to any fluid output from a wound, e.g., blood, serum, and/or pus, etc. As used herein, "fluid" generally refers to a liquid, a gas or both.

Referring to FIG. 1, a NPWT apparatus according to an embodiment of the present disclosure is depicted generally as 10 for use on a wound bed "w" surrounded by healthy skin "s". NPWT apparatus 10 includes a wound dressing 12 positioned relative to the wound bed "w" to define a vacuum chamber 14 about the wound bed "w" to maintain negative pressure at the wound area. Wound dressing 12 includes a contact layer 18, a wound filler 20 and a wound cover 24.

Contact layer 18 is intended for placement within the wound bed "w" and may be relatively non-supportive or flexible to substantially conform to the topography of the wound bed "w". A variety of materials may be used for the contact layer 18. Contact layer 18 selection may depend on various factors such as the patient's condition, the condition of the periwound skin, the amount of exudate and/or the condition of the wound bed "w". Contact layer 18 may be formed from perforated film material. The porous characteristic of the contact layer 18 permits exudate to pass from the wound bed "w" through the contact layer 18. Passage of wound exudate through the contact layer 18 may be substantially unidirectional such that exudate does not tend to flow back into the wound bed "w". Unidirectional flow may be encouraged by directional apertures, e.g., apertures positioned at peaks of undulations or cone-shaped formations protruding from the contact layer 18. Unidirectional flow may also be encouraged by laminating the contact layer 18 with materials having absorption properties differing from those of the contact layer 18, or by selection of materials that promote directional flow. A non-adherent material may be selected for forming the contact layer 18 such that the contact layer 18 does not tend to cling to the wound bed "w" or surrounding tissue when it is removed. One example of a material that may be suitable for use as a contact layer 18 is commercially available under the trademark XEROFLOW® offered by Tyco Healthcare Group LP (d/b/a Covidien). Another example of a material that may be suitable for use as the contact layer 18 is the commercially available CURITY® non-adherent dressing offered by Tyco Healthcare Group LP (d/b/a Covidien).

Wound filler 20 is positioned in the wound bed "w" over the contact layer 18 and is intended to transfer wound exudate. Wound filler 20 is conformable to assume the shape of any wound bed "w" and may be packed up to any level, e.g., up to the level of healthy skin "s" or to overfill the wound such that wound filler 20 protrudes over healthy skin "s". Wound filler 20 may be treated with agents such as polyhexamethylene biguanide (PHMB) to decrease the incidence of infection and/or other medicaments to promote wound healing. A variety of materials may be used for the wound filler 20. An example of a material that may be suitable for use as the wound filler 20 is the antimicrobial dressing commercially available under the trademark KERLIX™ AMD offered by Tyco Healthcare Group LP (d/b/a Covidien).

Cover layer 24 may be formed of a flexible membrane, e.g., a polymeric or elastomeric film, which may include a biocompatible adhesive on at least a portion of the cover layer 24, e.g., at the periphery 26 of the cover layer 24. Alternately, the cover layer 24 may be a substantially rigid member. Cover layer 24 may be positioned over the wound bed "w" such that a substantially continuous band of a biocompatible adhesive at the periphery 26 of the cover layer 24 forms a substantially fluid-tight seal with the surrounding skin "s". An example of a material that may be suitable for use as the cover layer 24 is commercially available under the trademark CURAFORM ISLAND® offered by Tyco Healthcare Group LP (d/b/a Covidien).

Cover layer 24 may act as both a microbial barrier and a fluid barrier to prevent contaminants from entering the wound bed "w" and to help maintain the integrity thereof.

In one embodiment, the cover layer 24 is formed from a moisture vapor permeable membrane, e.g., to promote the exchange of oxygen and moisture between the wound bed "w" and the atmosphere. An example of a membrane that may provide a suitable moisture vapor transmission rate (MVTR) is a transparent membrane commercially available under the trade name POLYSKIN®II offered by Tyco Healthcare Group LP (d/b/a Covidien). A transparent membrane may help to permit a visual assessment of wound conditions to be made without requiring removal of the cover layer 24.

Wound dressing 12 may include a vacuum port 30 having a flange 34 to facilitate connection of the vacuum chamber 14 to a vacuum system. Vacuum port 30 may be configured as a rigid or flexible, low-profile component and may be adapted to receive a conduit 36 in a releasable and fluid-tight manner. An adhesive on at least a portion of the underside of the flange 34 may be used to provide a mechanism for affixing the vacuum port 30 to the cover layer 24. The relative positions, size and/or shape of the vacuum port 30 and the flange 34 may be varied from an embodiment depicted in FIG. 1. For example, the flange 34 may be positioned within the vacuum chamber 14 such that an adhesive on at least a portion of an upper side surface of the flange 34 affixes the vacuum port 30 to the cover layer 24. A hollow interior portion of the vacuum port 30 provides fluid communication between the conduit 36 and the vacuum chamber 14. Conduit 36 extends from the vacuum port 30 to provide fluid communication between the vacuum chamber 14 and the vacuum source 40. Alternately, the vacuum port 30 may not be included in the dressing 12 if other provisions are made for providing fluid communication with the conduit 36.

Any suitable conduit may be used for the conduit 36, including conduit fabricated from flexible elastomeric or polymeric materials. In the NPWT apparatus 10 illustrated in FIG. 1, the conduit 36 includes a first conduit section 36A, a second conduit section 36B, a third conduit section 36C and a fourth conduit section 36D. The first conduit section 36A extends from the vacuum port 30 and is coupled via a fluid line coupling 100 to the second conduit section 36B, which extends to the collection canister 38. The third conduit section 36C extends from the collection canister 38 and is coupled via another fluid line coupling 100 to the fourth conduit section 36D, which extends to the vacuum source 40. The shape, size and/or number of conduit sections of the conduit 36 may be varied from the first, second, third and fourth conduit sections 36A, 36B, 36C and 36D depicted in FIG. 1.

The first, second, third and fourth conduit sections 36A, 36B, 36C and 36D of the conduit 36 may be connected to components of the apparatus 10 by conventional air-tight means, such as, for example, friction fit, bayonet coupling, or barbed connectors. The connections may be made permanent. Alternately, a quick-disconnect or other releasable connection means may be used to provide some adjustment flexibility to the apparatus 10.

Collection canister 38 may be formed of any type of container that is suitable for containing wound fluids. For example, a semi-rigid plastic bottle may be used for the collection canister 38. A flexible polymeric pouch or other hollow container body may be used for the collection canister 38. Collection canister 38 may contain an absorbent material to consolidate or contain the wound fluids or debris. At least a portion of canister 38 may be transparent. e.g. to permit a visual assessment of the wound exudate to assist in evaluating the color, quality and/or quantity of exudate. A transparent portion of the collection canister 38 may permit a visual assessment to assist in determining the remaining capacity or open volume of the canister and/or may assist in determining whether to replace the collection canister 38.

The collection canister 38 is in fluid communication with the wound dressing 12 via the first and second conduit sections 36A, 36B. The third and fourth conduit sections 36C, 36D connect the collection canister 38 to the vacuum source 40 that generates or otherwise provides a negative pressure to the collection canister 38. Vacuum source 40 may include a peristaltic pump, a diaphragmatic pump or other suitable mechanism. Vacuum source 40 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg to about 125 mmHg, or about 40 mmHg to about 80 mmHg. One example of a peristaltic pump that may be used as the vacuum source 40 is the commercially available Kangaroo PET Eternal Feeding Pump offered by Tyco Healthcare Group LP (d/b/a Covidien). Vacuum source 40 may be actuated by an actuator (not shown) which may be any means known by those skilled in the art, including, for example, alternating current (AC) motors, direct current (DC) motors, voice coil actuators, solenoids, and the like. The actuator may be incorporated within the vacuum source 40.

In embodiments, the NPWT apparatus 10 includes one or more fluid line couplings 100 that allow for selectable coupling and decoupling of conduit sections. For example, a fluid line coupling 100 may be used to maintain fluid communication between the first and second conduit sections 36A, 36B when engaged, and may interrupt fluid flow between the first and second conduit sections 36A, 36B when disengaged. Thus, fluid line coupling 100 may facilitate the connection, disconnection or maintenance of components of the NPWT apparatus 10, including the replacement of the collection canister 38. Additional or alternate placement of one or more fluid line couplings 100 at any location in line with the conduit 36 may facilitate other procedures. For example, the placement of a fluid line coupling 100 between the third and fourth conduit sections 36C, 36D, as depicted in FIG. 1, may facilitate servicing of the vacuum source 40.

Figure 2:
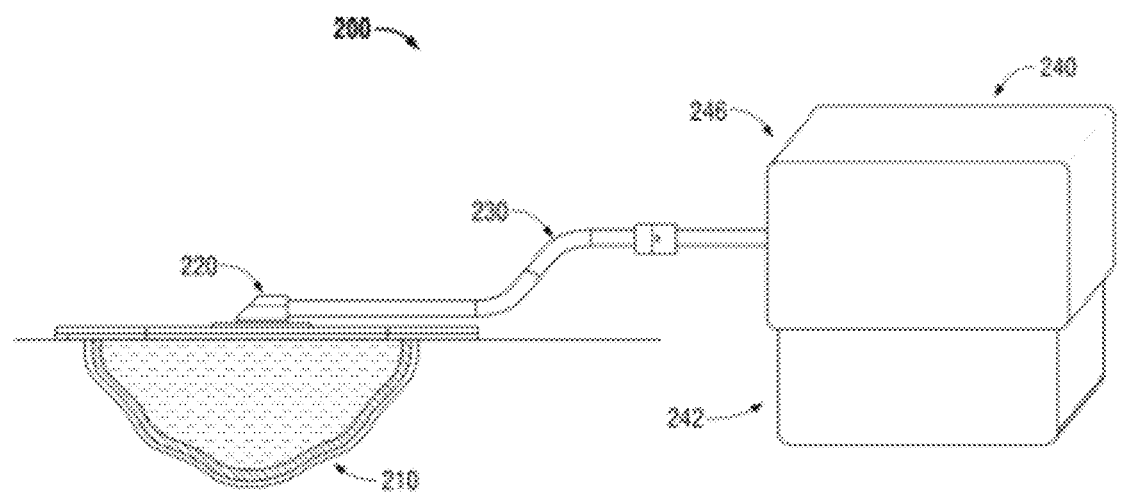
FIG. 2 is a diagram of an embodiment of a NPWT system in accordance with the present disclosure.

Referring to FIG. 2, the NPWT system shown generally as 200 can be worn by a patient or user and includes a dressing assembly 210, a wound port assembly 220, an extension assembly 230 and a canister assembly 240. Dressing assembly 210 is positioned relative to the wound area to define a vacuum chamber about the wound area to maintain negative pressure at the wound area. Dressing assembly 210 may be substantially sealed from extraneous air leakage, e.g., using adhesive coverings. Wound port assembly 220 is mounted to the dressing assembly 210. For example, wound port assembly 220 may include a substantially continuous band of adhesive at its periphery for affixing the wound port assembly 220 to the dressing assembly 210. Extension assembly 230 is coupled between the wound port assembly 220 and the canister assembly 240 and defines a fluid flow path between the wound port assembly 220 and the canister assembly 240. A hollow interior of the wound port assembly 220 provides fluid communication between the extension assembly 230 and the interior of the dressing assembly 210. Dressing assembly 210 and the wound port assembly 220 shown in FIG. 2 are similar to components of the wound dressing 12 of FIG. 1 and further description thereof is omitted in the interests of brevity.

Canister assembly 240 includes a control unit 246 and a collection canister 242 disposed below the control unit 246. Control unit 246 may be reusable and collection canister 242 may be disposable. Control unit 246 and the collection canister 242 may be releasably coupled. Mechanisms for selective coupling and decoupling of the control unit 246 and the collection canister 242 include fasteners, latches, clips, straps, bayonet mounts, magnetic couplings, and other devices. Collection canister 242 may consist of any container suitable for containing wound fluids.

In one embodiment, the NPWT system 200 is capable of operating in a continuous mode or an alternating mode. In the continuous mode, the control unit 246 controls a pump to continuously supply a selected vacuum level at the collection canister 242 to create a reduced pressure state within the dressing assembly 210. In the alternating mode, the control unit 246 controls the pump to alternating supply a first negative pressure, e.g., about 80 mmHg, at the collection canister 242 for a preset fixed amount of time and a second negative pressure, e.g., about 50 mmHg, at the collection canister 242 for a different preset fixed amount of time.

In general, the output of the pump is directly related to the degree of air leakage in the NPWT system 200 and the open volume in the collection canister 242. If there is sufficient air leakage in the system 200, e.g., at the dressing assembly 210, the pump can remain on continuously and the control unit 246 can control negative pressure at the collection canister 242 by adjusting the pump speed. Alternatively, if there is not sufficient air leakage in the system 200 to permit the pump to remain on continuously, the control unit 246 can control negative pressure at the collection canister 242 by turning the pump on and off, e.g., for non-equal on/off periods of time.

Canister assembly 240 may be constructed from a variety of materials such as Lucite™ polycarbonate, metals, metal alloys, plastics, or other durable materials capable of withstanding forces applied during normal use, and may have some capability of withstanding possibly excessive forces resulting from misuse. Collection canister 242 may include a window with fluid level markings or for promoting visual assessment of the amount of exudate contained within the collection canister 242. A transparent or partially transparent collection canister 242 may thus assist in determining the remaining capacity of the collection canister 242 and/or when the collection canister 242 should be replaced.

Figure 3:
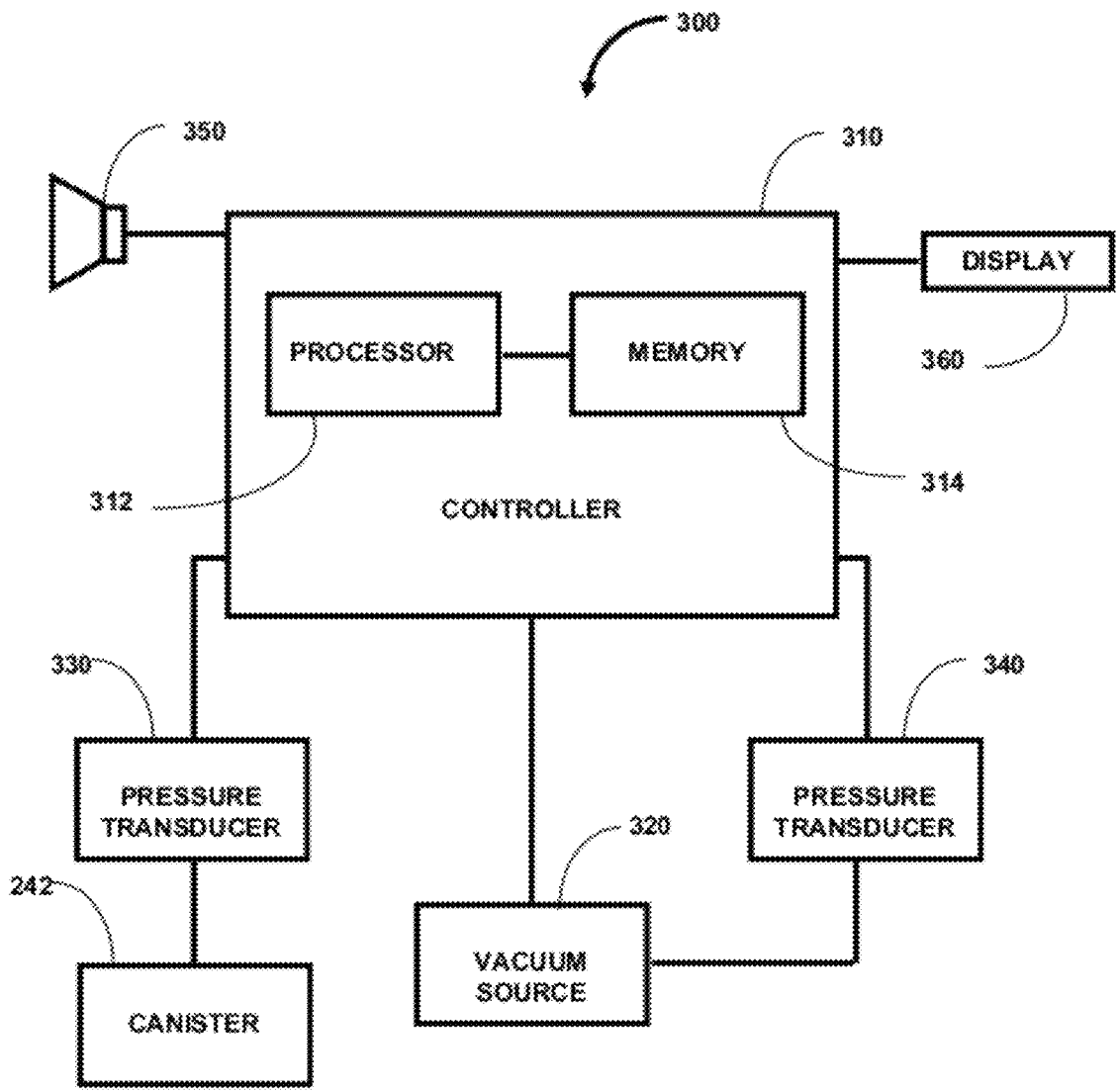
FIG. 3 is a system diagram of a control system for a NPWT system in accordance with the present disclosure.

Referring to FIG. 3, the NPWT device has a control system generally shown as 300. Control system 300 may include a controller 310 that controls the operation of the NPWT device. Controller 310 may include at least one processor 312 and at least one memory module 314. The memory module 314 may be a volatile memory (e.g. DRAM, SRAM, or the like) or a non-volatile memory (e.g., ROM, PROM, EPROM, EEPROM, a semiconductor flash memory, or the like). The memory module 314 stores instructions that are executed by the processor 312 for controlling the NPWT device.

Controller 310 controls a vacuum source 320 based on the mode of therapy selected as well as inputs received from pressure transducer 330 and pressure transducer 330. Vacuum source 320 may be a miniature pump or micropump that may be biocompatible and adapted to maintain or draw adequate and therapeutic vacuum levels. The vacuum level of subatmospheric pressure achieved may be in the range of about 20 mmHg to about 500 mmHg. In embodiments, the vacuum level may be about 75 mmHg and about 125 mmHg, or between about 30 mmHg and 80 mmHg. Vacuum source 320 is actuated by an actuator which may be any means known by those skilled in the art, including, for example, AC motors, DC motors, voice coil actuators, solenoids, etc.

Controller 310 maintains a selected vacuum level at the canister 242 by monitoring the pressure in the canister 242 using pressure transducer 330. If the vacuum level in the canister 242 exceeds a threshold as measured by pressure transducer 340, the controller 310 turns the vacuum source 320 off or reduces the output of the vacuum source 320 to reduce the vacuum level in the canister 242. If the vacuum level in the canister 242 falls below a threshold as measured by pressure transducer 340, the controller 310 turns the vacuum source 320 on or increases the output of the vacuum source 320 to increase the vacuum level in the canister 242.

Controller 310 also controls operation of the vacuum source 320 based on the output of pressure transducer 340. Pressure transducer 340, which could be a pressure switch, monitors the pressure at the inlet of the vacuum source 320 to determine a pressure spike indicative of the replace canister condition which will be described in more detail below. Alternately, if a pressure switch is used, once a threshold of negative pressure is reached, it will actuate thereby signaling the controller 310 to turn the vacuum source 320 off.

Control system 300 may include a speaker 350 to produce an audible indication to notify the user of a condition, e.g., leak, canister assembly tip, failed pressure sensor, failed pump, excessive vacuum, or low battery conditions. The control system 300 may also include a display 360 to notify a user of an alarm condition, a state of the NPWT device, or other information related to the treatment of a wound by the NPWT device. Display 360 may be a liquid crystal display (LCD), a light emitting diode (LED) display, or any number of LEDs, neon lamps, incandescent bulbs, or the like.

Control system 300 responds to various sensed events by signaling alarms. Various types of conditions may be signaled by alarms. In embodiments, control system 300 is capable of signaling alarms for failed pressure sensor condition, use odometer expired condition, watchdog reset condition, failed pump condition, leak condition, replace canister condition, excessive vacuum condition, failed LEDs condition, low battery condition, very low battery condition, and failed battery condition. Priority levels may be associated with alarms. In embodiments, the priority levels of alarms are low priority alarm, medium priority alarm, and system alarm (highest priority). Low priority alarms, when triggered, may be continuously indicated. Medium priority alarms and system alarms, when triggered, may have a flashing indication.

Control system 300 may stop operation of the in response to an alarm, e.g., depending on alarm type and/or priority level. In embodiments, the control system 300 stops operation of the pump in response to system alarms, e.g., failed pressure sensor system alarm, use odometer expired system alarm, watchdog reset system alarm, failed pump system alarm, excessive vacuum system alarm, and/or failed LEDs system alarm.

If an air leak develops in the NPWT system 200, e.g., at the dressing assembly 210, for which the control unit 246 cannot compensate by increasing the pump speed, the control system 300 may indicate an alarm. For example, the control system 300 may indicate a leak alarm after two consecutive minutes of operation in which the vacuum level is below the current set point (or below the minimum level of a set point range).

In embodiments, the control system 300 includes a user interface (not shown) which may be incorporated into the display 360 or may be a set of user actuated switches or buttons. The user turns ON the canister assembly 240 by pressing a power button (not shown). When the power button is pressed, the control system 300 performs a series of internal checks during power up. In one embodiment, after successfully completing the power-up tasks, the control system 300 turns on the pump 320 using the stored settings. At initial activation of the canister assembly 240, the stored settings are the default settings. In one embodiment, the default settings for controlling the pump 320 are 80 mmHg and continuous mode. In one embodiment, the currently stored vacuum level setting can be altered by the user, e.g., to 50 mmHg. In one embodiment, the currently stored mode setting can be altered by the user, e.g., to an alternating mode.

Figures 4A, 4B:
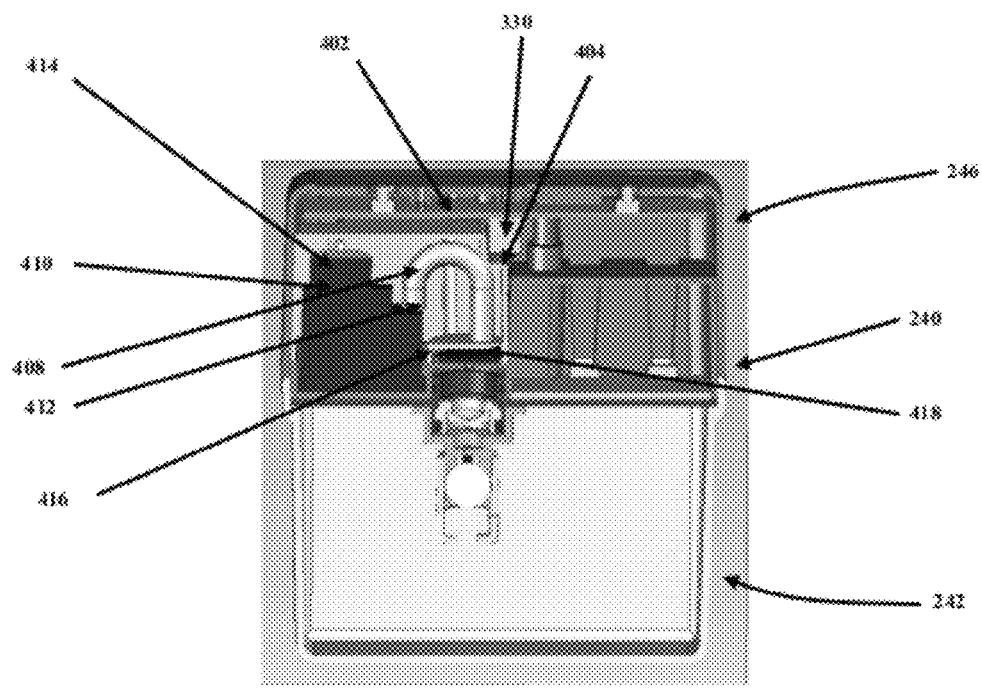
FIG. 4A is a diagram of a canister assembly for a NPWT system in accordance with the present disclosure.
FIG. 4B is a diagram of a canister assembly for a NPWT system in accordance with the present disclosure.

Referring to FIGS. 4A and 4B, the two cross-sectional views of a canister assembly 240 illustrate the electronic, electrical and pneumatic components of a NPWT device in accordance with an embodiment of the present disclosure. At the top portion of the control unit 246, immediately below a user interface (not shown), is a printed circuit board (PCB) 402. Pressure transducer 330 is attached to the PCB 402. The controller 310 includes circuits that power the pressure transducer 330 and receive its pressure signals (i.e., electrical signals indicative of the negative pressure being measured). The PCB 402 includes signal processing circuits that condition the signals, including filtering to reject electrical noise and provide a clean signal to the controller 310.

Pressure transducer 330 has a hydrophobic filter at area 404, which protects the pressure transducer 330 if exudate fluid entered a pressure transducer tube (not shown). The pressure transducer is attached to the hydrophobic filter at area 404 and the opposite end of the pressure transducer tube attaches to a transducer port 503 (shown in FIG. 5), at the bottom of the control unit 246. The tube is fit by friction. The transducer port 503 at the bottom of the control unit 246 pneumatically communicates with the canister 242 through the canister transducer port 604 (shown in FIG. 6), when the canister 242 is attached to the control unit 246. The pressure transducer 330 directly monitors the vacuum level at the canister transducer port 604.

A pressure transducer 340 (shown in FIG. 4B), which could be a pressure switch, may also be attached to the PCB 402. The pressure transducer 340 has its own set of signal conditioning circuits in controller 310 as may be required. A pressure transducer tube 340T is attached to the neck of the pressure transducer 340. The other end of the pressure transducer tube 340T is attached to the pump inlet tube 408 (shown in FIG. 4A). The pressure transducer 340 monitors the pressure at the pump inlet 412 to determine a pressure spike indicative of the replace canister condition which will be described below.

A direct current (DC) motor-driven pump 410 is contained within the control unit 246. A vibration damping tape, e.g., visco-elastic damping tape, may be applied to the outer surface of the pump 410 to reduce vibration and its associated noise. The pump 410 may be contained within its own sub-housing 414 which may be hollow or formed entirely of open cell molded foam, e.g., used as a silencer to provide sound mitigation by reducing the sound energy of the expelled air during operation. As part of the sound mitigation arrangement, a tube may be fitted to the pump sub-housing 414.

A pump inlet tube 408 is attached on one end to the inlet port 412 of the pump 410 on one end. The other end of the pump inlet tube 408 attaches to the filter assembly 416. The filter assembly 416 has an orifice 418. A suction chamber is located directly below the filter assembly 416 that receives the canister suction port 601 (shown in FIGS. 6 & 7) when the canister 242 is attached to the control unit. 246.

Figure 5:
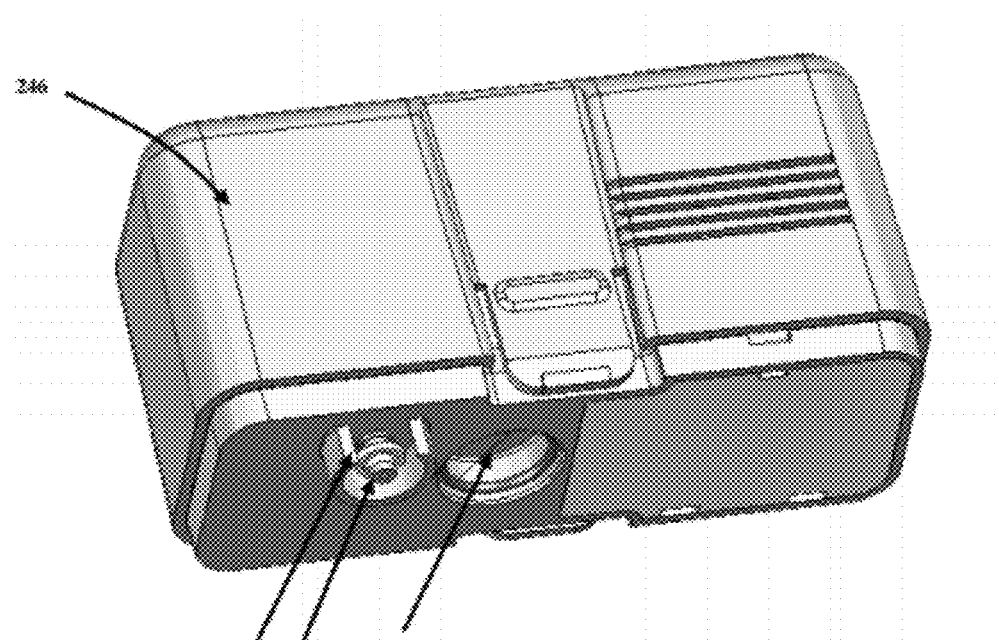
FIG. 5 is a diagram of a control unit for a NPWT system in accordance with the present disclosure.

FIG. 5 is a view of the bottom portion of the control unit 246 and illustrates a control unit suction port 504 and a control unit transducer port 503. Control unit suction port 504 is connected internally to the pump 510. The control unit transducer port 503 is connected internally to the pressure transducer 330. Associated with the control unit transducer port 503 is a protrusion 505 which interfaces with the canister transducer port 604, which pushes open a silicone valve 420 (shown in FIG. 4B).

Figure 6:
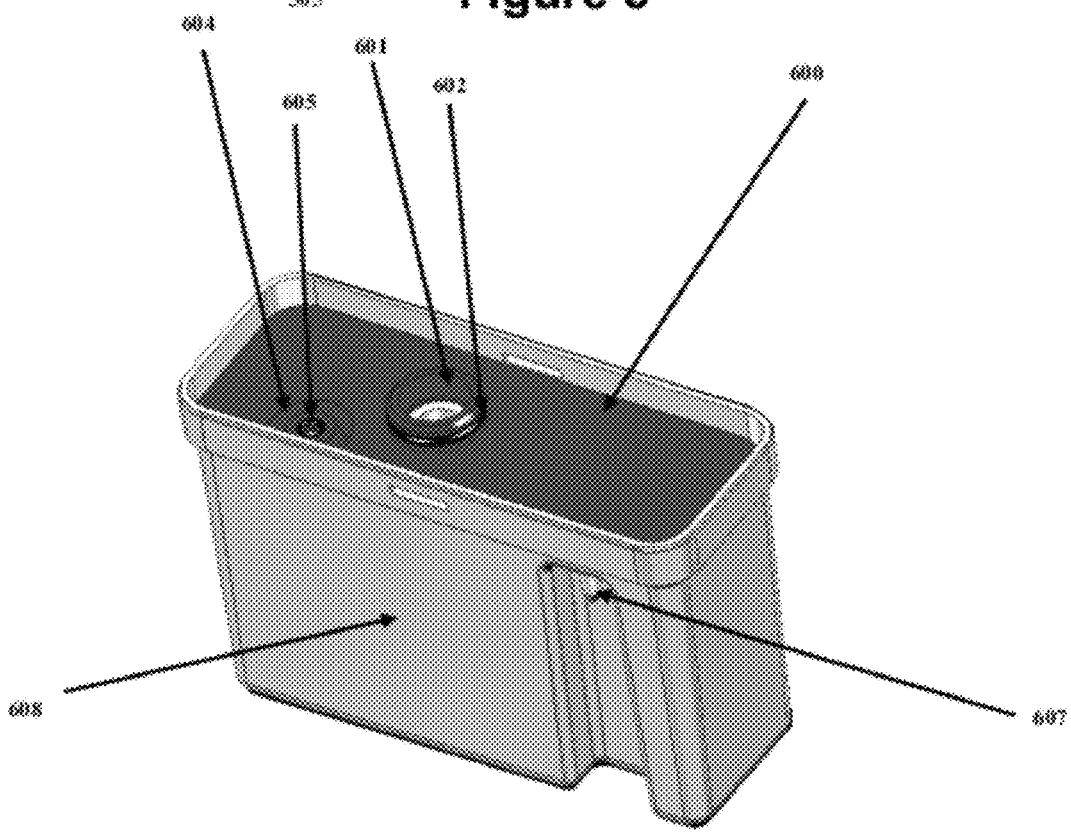
FIG. 6 is a diagram of a collection canister for a NPWT system in accordance with the present disclosure.

FIG. 6 illustrates the canister top 600 which encloses the open volume of the canister 242. In FIG. 6, the canister top 600 is depicted in the assembled condition with respect to the canister 242. The canister top 600 includes a canister suction port 601 and a canister transducer port 604. The canister suction port 601 and the canister transducer port 604 include respective o-rings 602, 605 which are received within the respective control unit suction port 504 and the control unit transducer port 503 of the control unit (FIG. 5) in fluid tight relation when the control unit 246 is mounted to the canister top 600. The canister top 600 further includes a wound exudate port 607 extending into the open volume portion 608 of the canister 242 in fluid communication with extension assembly 230 to receive exudate from the wound.

Figure 7A:
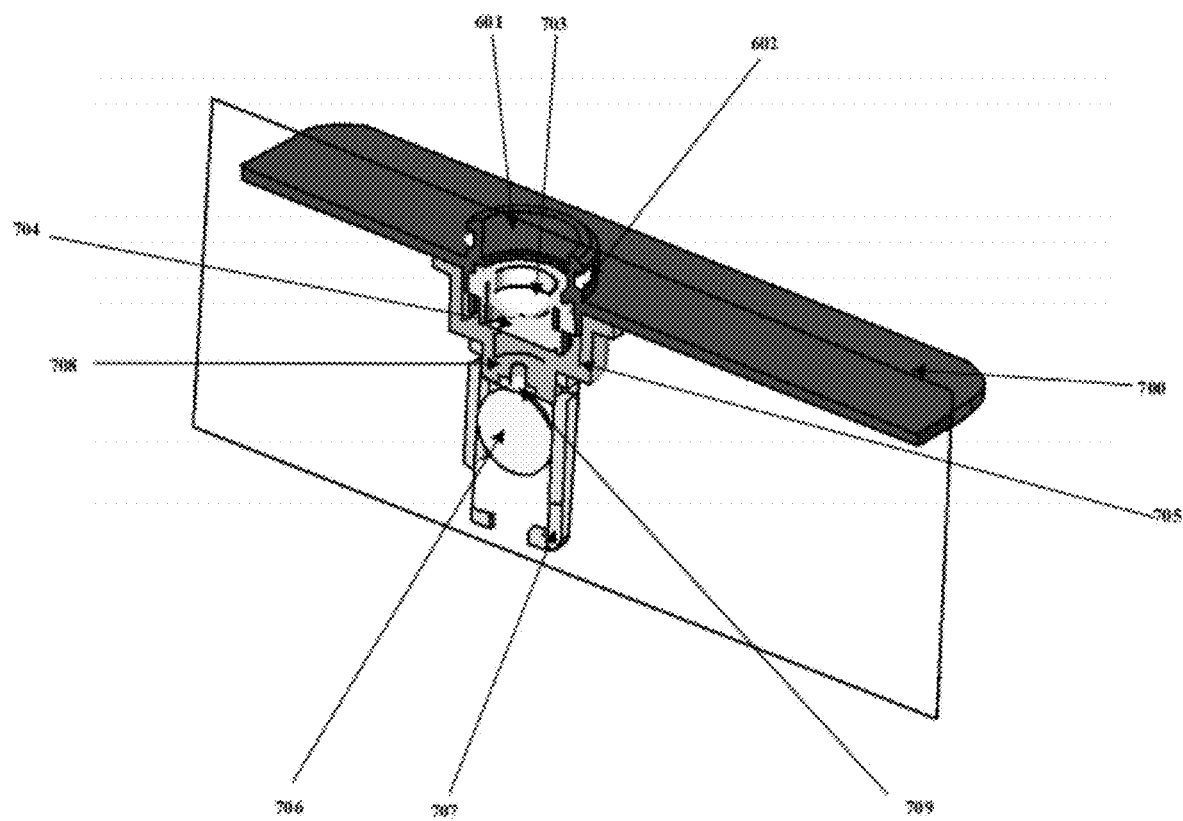
FIG. 7A is a diagram of a collection canister for a NPWT system in accordance with the present disclosure.

FIG. 7A illustrates the bottom portion 700 of canister top 600. The bottom portion 700 contains a suction port 601 with an o-ring 602 as discussed before. A silicone valve 703, also known as a rolling sleeve valve, may be located at the bottom of the suction port 601. Below the silicone valve 703, is a splash guard 704, which restricts contact of fluid with the silicone valve 703 if the canister 242 is tipped or shaken while not attached to the control unit 246. A ball seat housing 705 is below the splash guard 704, further protecting the silicone valve and also providing an attachment point to the ball cage 707. Inside of the ball seat housing 705 is a recess that receives the ball seat 708. An orifice 709 is centered in the ball seat 708 embedded in the ball seat housing. To prevent encrustation of bottom portion 700 and all associated parts by the drying exudate, a coating may be applied to the components, which inhibit this encrustation by affecting the formation and binding of proteins or may decrease wetability to allow liquid to shed. In conjunction with the splash guard 704 a second layer may be added to it on the exudate side facing the open volume canister that is permeable and does not allow exudate to encrust upon it. Encrustation of the membrane inhibits air flow through it.

When the ball float 706 contacts the seat 708, air flow to the pump 410 is blocked while the pump 410 continues to run, thereby producing the pressure spike mentioned, which indicates the replace canister condition. A fixed leak is incorporated either into the pump 410 or to the pump inlet tube 408, which is meant to relieve the negative pressure at the pump inlet and at the floating ball seat 708, so that the floating ball 706 can fall out of the sealing position.

Figure 7B:
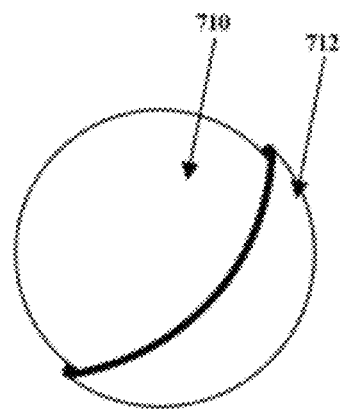
FIGS. 7B-7F are a diagrams of a ball floats for a NPWT system in accordance with the present disclosure

FIGS. 7B through 7F depict examples of ball floats that may be used in the NPWT device according to an embodiment of the present disclosure. To prevent encrustation of the ball float by the drying exudate, a coating 712 may be applied to the ball float 710 (as shown in FIG. 7B), which inhibit this encrustation by affecting the formation and binding of proteins or may decrease wetability to allow liquid to shed. Coating 712 may be made from a hydrophobic material, latex or TEFLON®, or the like.

Figure 7C:
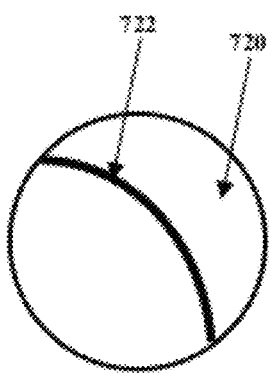
Figure 7D:
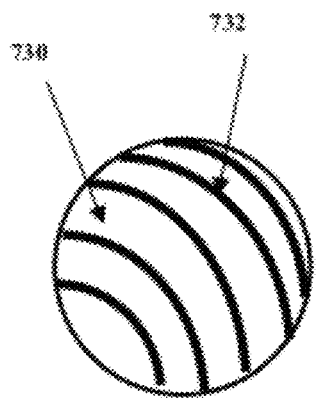
Figure 7E:
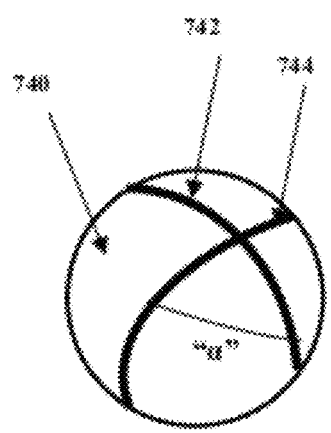
Figure 7F:
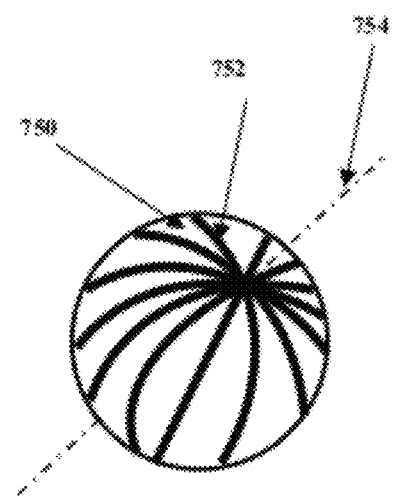

FIG. 7C depicts a ball float 720 having a groove or track 722 running along the center of the ball float 720. Groove 722 could be a straight line or a wavy line. FIG. 7D depicts a ball float 730 having multiple grooves or tracks 732. Grooves 732 may be arranged in concentric circles around to the ball float 730. The distance between each concentric circle may be constant or may vary. FIG. 7E depicts a ball float 740 having a first groove or track 742 and a second groove or track 744. Groove 742 and groove 744 intersect each other at two points on ball float 740. The angle "α" between groove 742 and groove 744 can range from greater than 0° to less than 180°. FIG. 7F depicts a ball float 750 having multiple grooves 752. Grooves 752 may be spaced evenly around the ball float or spaced at varying degrees. Grooves 752 intersect each other at an axis of the ball float 750 generally shown as 754.

Figure 8:
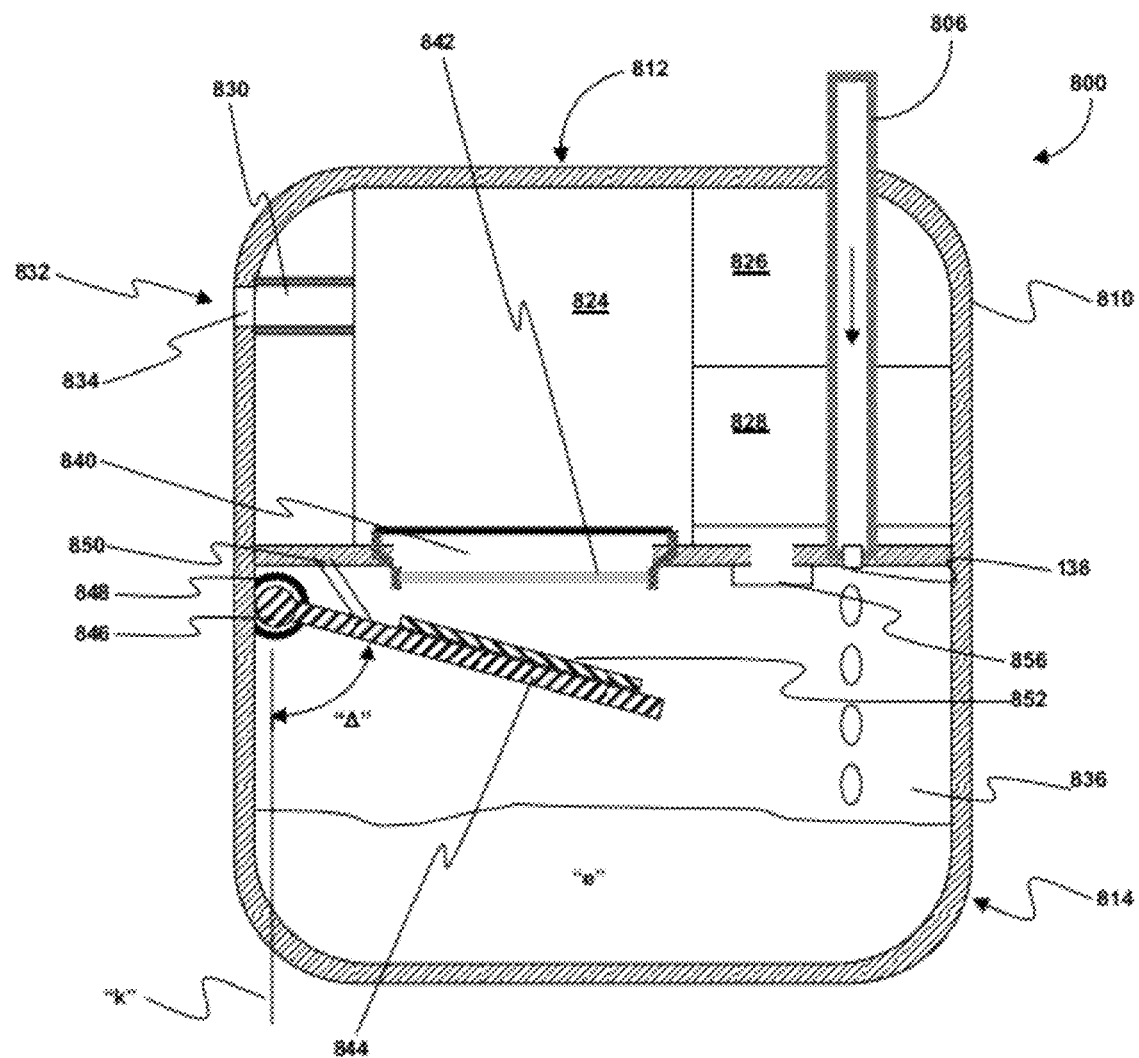
FIG. 8 is a diagram of a canister assembly for a NPWT system in accordance with the present disclosure.
Figure 9:
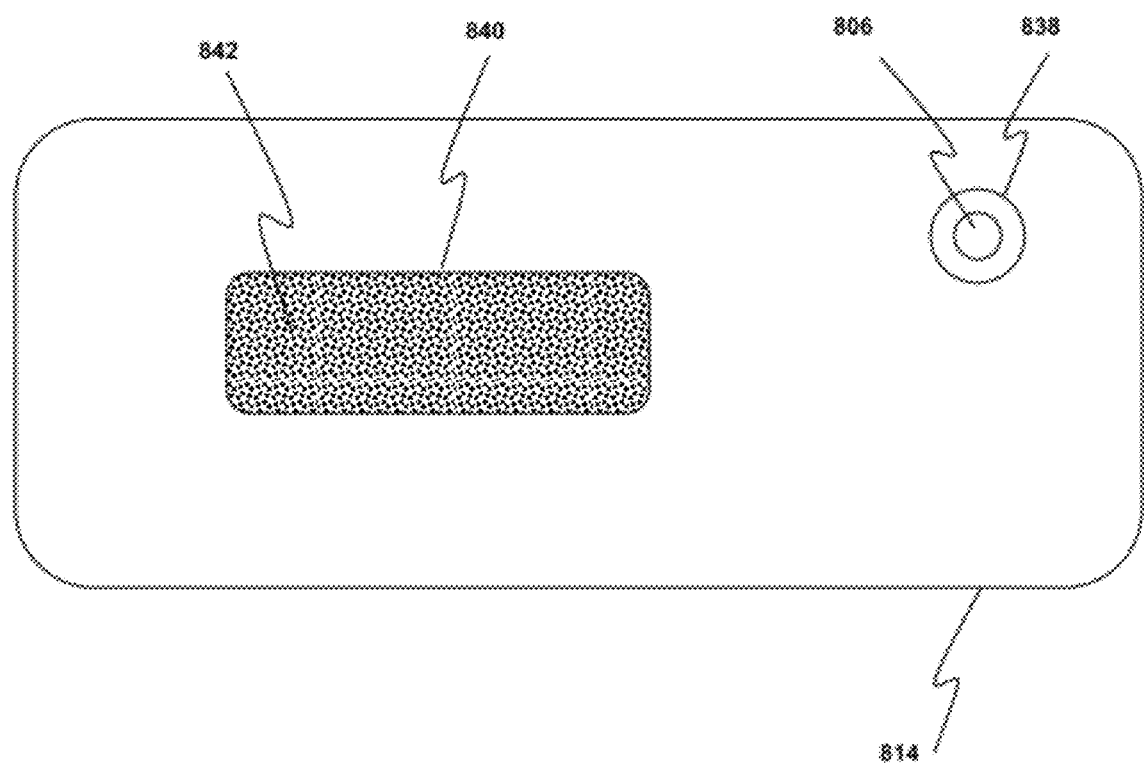
FIG. 9 is a top view of a collection canister for a NPWT system in accordance with the present disclosure.

FIGS. 8 and 9 illustrate a canister assembly 800 in accordance with an embodiment of the present disclosure. Canister assembly 800 includes housing 810, control unit 812 disposed within the housing 810 and collection canister 814. Housing 810 may be any suitable rigid member adapted for donning by the subject. Control unit 812 may incorporate vacuum source or pump 824, actuator or motor 826 for activating the vacuum source 824 and power source 828. Vacuum source 824 generates or otherwise provides negative pressure to the wound.

Power source 828 may be disposed within housing 810 or separately mountable to the housing 810. A suitable power source 828 includes alkaline batteries, wet cell batteries, dry cell batteries, nickel cadmium batteries, solar generated means, lithium batteries, NiMH batteries (nickel metal hydride) each of which may be of the disposable or rechargeable variety.

Housing 810 further includes vent portal 830 configured to vent exhaust air from vacuum source 824 through exhaust port 832. Vent portal 830 extends from housing 810 and may be directly connected to vacuum source 824. It is also envisions that vent portal 830 may exhaust air from within housing 810 rather than directly from vacuum source 824. Exhaust port 832 may include filter 834 extending across the exhaust port 832. Filter 834 may be a bacterial filter to prevent emission of bacteria from housing 810.

Collection canister 814 collects exudates "e" removed from the wound bed "w" during therapy through conduit, or tubing, 806. Collection canister 814 is associated with housing 810 and may be incorporated within the housing 810 or releasably connected to the housing 810 by conventional means. Housing 810 and collection canister 814 of canister assembly 800 may be releasably coupled. Mechanisms for selective coupling and decoupling of housing 810 and collection canister 814 include fasteners, latches, clips, straps, bayonet mounts, magnetic couplings, and other devices.

Collection canister 814 may comprise any container suitable for containing wound fluids and is substantially rigid defining an internal chamber 836 in fluid communication with tubing 806. Collection canister 814 may contain an absorbent material to consolidate or contain the wound drainage or debris. In embodiments, at least a portion of collection canister 814 may be transparent to assist in evaluating the color, quality, or quantity of wound exudates. A transparent canister may thus assist in determining the remaining capacity of the canister or when the canister should be replaced. In the alternative, collection canister 814 may be relatively flexible.

Collection canister 814 includes fluid inlet 838 and suction port 840. Fluid inlet 838 is configured to operably engage conduit 806. Fluid inlet 838 may be connectable with conduit 806 by conventional air and fluid tight means, such as those described above. In embodiments, fluid inlet 838 may contain a luer lock or other connector within the purview of those skilled in the art to secure the end of conduit 806 with the fluid inlet 838. It is envisioned that fluid inlet 838 is configured to receive a cap in order to prevent leakage of exudates and odor from internal chamber 836 of collection canister 814 when housing 810 is separated from the canister 814.

Suction port 840 is in fluid communication with vacuum source 824 and may be an opening defined in a wall of housing 810. A filter 842, such as a hydrophobic membrane or baffling to prevent exudates from being aspirated into pump 810 may be disposed adjacent or within suction port 840. Filter 842 may also include charcoal or other odor absorbing materials and may prevent the passage of bacteria. Pump 824 creates a vacuum within internal chamber 836 of collection canister 832 by drawing air through suction port 840.

Collection canister 814 includes closure valve 844. Closure valve 844 is pivotally mounted about hinge 846 which is connected to internal chamber surface of collection canister 814. Closure valve 844 assumes the open position depicted in FIG. 8 when collection canister 814 is upright and not filled with exudates "e". Specifically, the gravitational weight of closure valve 844 will ensure that the closure valve is pivoted to the open condition in the presence of the aforedescribed conditions. As an alternative, closure valve 844 also may be resiliently biased to the open position depicted as in FIG. 8. Means for biasing closure valve 844 are envisioned including a torsion spring 848 mounted about hinge 846 and operatively engageable with the closure valve 844. In the alternative, a leaf spring 850 may be connected to an interior surface of canister 814 and extend into engagement with closure valve 844 to normally bias the closure valve 844 to the open position. In embodiments, closure valve 844 is at a predetermined angle "A" when in the fully open position. Angle may range from about 10° to about 70° relative to the longitudinal axis "k" of collection canister 814. Closure valve 844 is of sufficient weight or mass to remain in the open condition even in the presence of a vacuum draw generated during operation of pump 824.

Figure 10:
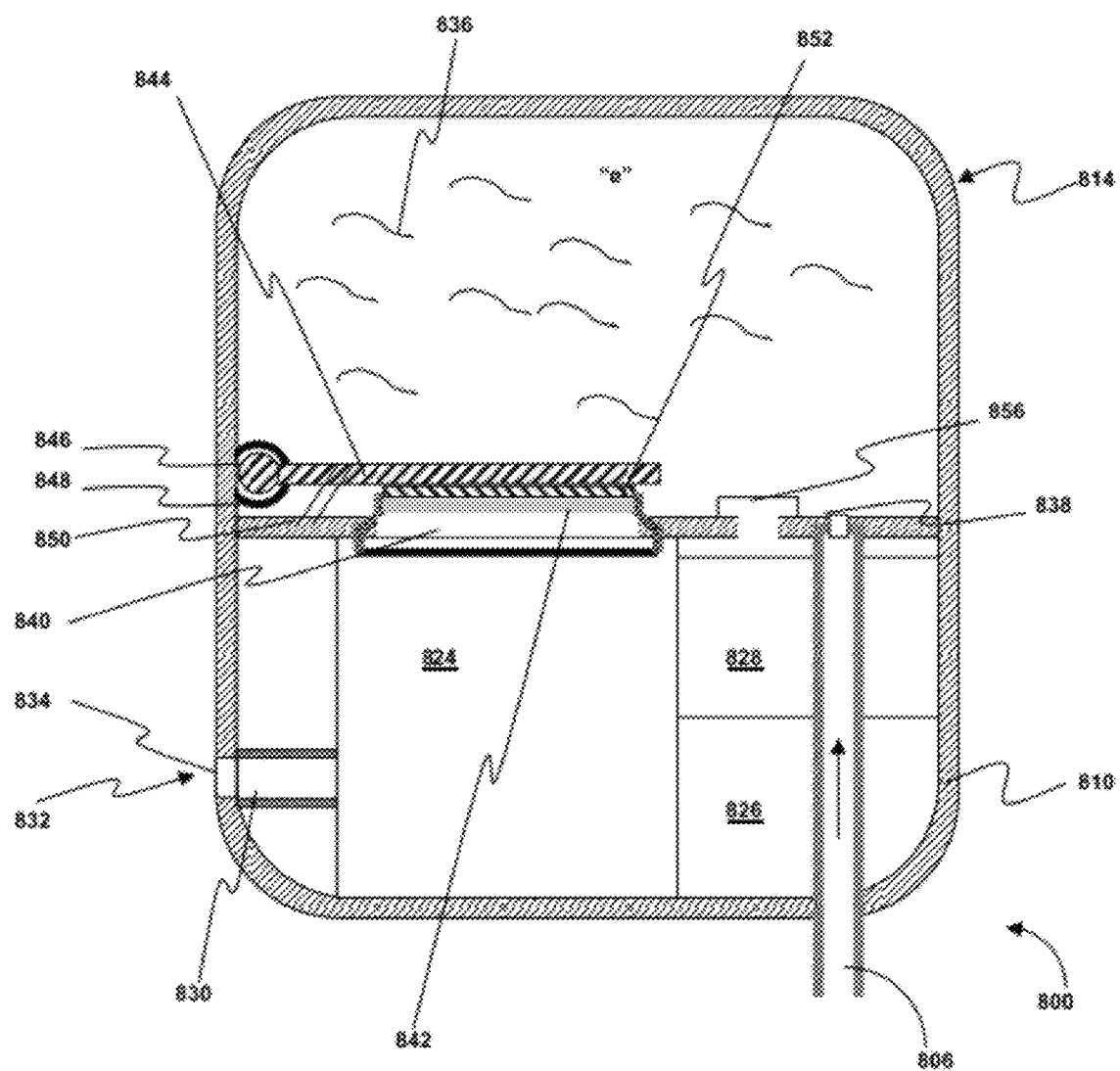
FIG. 10 is a diagram of a canister assembly for a NPWT system in accordance with the present disclosure.

Closure valve 844 prevents exudates from clogging and/or entering pump 824 or control unit 812 when collection canister 814 is in an inverted or a tilted position. For example, when collection canister 844 is tilted beyond a predetermined orientation, e.g., when on its side or inverted with suction port 840 facing in a general downward direction, closure valve 844 moves under its own weight, the weight of exudates, and/or gravity to a closed position. Moreover, when tilted or inverted, closure valve 844 defines a moment arm thereby causing the closure valve 844 to pivot about hinge 846 from the open position to the closed position (FIG. 10). The moment arm defined by closure valve 844 may be altered by adjusting the length or weight of the closure valve 844.

In the closed position of FIG. 10, closure valve 844 seals suction port 840 thereby sealing the exudates "e" within canister 814 and/or preventing clogging of filter 842. It is envisioned that closure valve 844 may define seat 852 which resides within suction port 844 in sealed engagement with the wall surfaces defining the suction port 840. Seat 852 may include an elastomeric member to facilitate formation of a seal between the two components. In the closed position, a vacuum change (e.g., drop in vacuum) will alert the subject of the disoriented canister. The vacuum change may be identified or recognized by the user through increased noise or churning of the vacuum source 824. In the alternative, a pressure transducer 856 may be in communication with internal chamber 836 to detect changes in pressure. Logic associated with transducer 856 and vacuum source 824 may reduce the speed of vacuum source 824 or stop operation of the vacuum source 824.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A portable negative pressure wound therapy system comprising:
    a dressing assembly for positioning over a wound to apply a negative pressure to the wound; and
    a canister assembly dimensioned to be worn by a user, said canister assembly including:
        a control unit having a negative pressure source and a controller; and
        a collection canister in communication with the dressing assembly and having a chamber operable to receive fluid from the wound, the collection canister including:
            a suction port in fluid communication with said negative pressure source; and
            a ball float arrangement having a ball float operable to substantially close said suction port in response to one of collection of a predetermined volume of exudate in the collection canister, tilting of the collection canister beyond a predetermined angle of orientation or inversion of the collection canister, wherein said ball float has at least one groove.

2. The portable negative pressure wound therapy system according to claim 1, wherein said control unit further comprises a pressure transducer operable to measure a pressure level in said collection canister.

3. The portable negative pressure wound therapy system according to claim 2, wherein said pressure transducer provides a signal to said controller based on the measured pressure level and said controller controls said negative pressure source based on the signal.

4. A portable negative pressure wound therapy system comprising,
    a dressing assembly for positioning over a wound to apply a negative pressure to the wound; and
    a canister assembly dimensioned to be worn by a user, said canister assembly including:

a control unit having a negative pressure source, a controller, and a pressure transducer operable to measure a pressure level in said collection canister; and a collection canister in communication with the dressing assembly and having a chamber operable to receive fluid from the wound, the collection canister including:

a suction port in fluid communication with said negative pressure source; and a ball float arrangement having a ball float operable to substantially close said suction port in response to one of collection of a predetermined volume of exudate in the collection canister, tilting of the collection canister beyond a predetermined angle of orientation or inversion of the collection canister, wherein said control unit further comprises a first transducer port coupled to said pressure transducer, said first transducer port has a protrusion coupled thereto; and said collection canister has a second transducer port, said second transducer port having a valve to prevent exudate from exiting said collection canister, said protrusion opens said valve when said control unit is attached to said collection canister so that said pressure transducer can measure the pressure level in said collection canister.

5. The portable negative pressure wound therapy system according to claim 1 further comprising a pressure transducer operable to measure a pressure level at an inlet of said negative pressure source, said pressure transducer measures an increase in the pressure level when said ball float closes said suction port and said controller turns off or reduces an output of said negative pressure source based on the measured increase in the pressure level.

6. The portable negative pressure wound therapy system according to claim 5, wherein said pressure transducer is a pressure switch.

7. The portable negative pressure wound therapy system according to claim 1, wherein said ball float assembly having said ball float includes a ball seat housing coupled to said suction port, said ball seat housing having a ball seat in fluid communication with said suction port, said ball float rests in said ball seat when said predetermined volume of exudate in the collection canister is collected.

8. The portable negative pressure wound therapy system according to claim 6 further comprising a ball cage coupled to said ball seat housing, said ball float being housed in said ball cage.

9. A portable negative pressure wound therapy system comprising, a dressing assembly for positioning over a wound to apply a negative pressure to the wound; and a canister assembly dimensioned to be worn by a user, said canister assembly including:

a control unit having a negative pressure source and a controller; and a collection canister in communication with the dressing assembly and having a chamber operable to receive fluid from the wound, the collection canister including:

a suction port in fluid communication with said negative pressure source; and a ball float arrangement having a ball float operable to substantially close said suction port in response to one of collection of a predetermined volume of exudate in the collection canister, tilting of the collection canister beyond a predetermined angle of orientation or inversion of the collection canister, wherein said ball float has a coating, said coating includes a hydrophobic material, latex, or polytetrafluoroethylene (PTFE).

10. The portable negative pressure wound therapy system according to claim 1, wherein said control unit is reusable.

11. The portable negative pressure wound therapy system according to claim 1, wherein said collection canister is disposable.

* * * * *